United States Patent
Bray

(10) Patent No.: US 10,590,126 B2
(45) Date of Patent: Mar. 17, 2020

(54) NON-SELECTIVE PROTEASE ACTIVATED RECEPTOR 4 ALA120THR ISOFORM ANTAGONIST

(71) Applicant: THOMAS JEFFERSON UNIVERSITY, Philadelphia, PA (US)

(72) Inventor: Paul F. Bray, Penn Valley, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 0 days.

(21) Appl. No.: 15/768,329

(22) PCT Filed: Oct. 14, 2016

(86) PCT No.: PCT/US2016/057169
§ 371 (c)(1),
(2) Date: Apr. 13, 2018

(87) PCT Pub. No.: WO2017/066661
PCT Pub. Date: Apr. 20, 2017

(65) Prior Publication Data
US 2018/0297996 A1 Oct. 18, 2018

Related U.S. Application Data

(60) Provisional application No. 62/242,114, filed on Oct. 15, 2015.

(51) Int. Cl.
| | |
|---|---|
| *C07D 471/04* | (2006.01) |
| *A61P 9/10* | (2006.01) |
| *C07D 209/12* | (2006.01) |
| *C07D 209/14* | (2006.01) |
| *C07D 401/04* | (2006.01) |
| *A61K 31/437* | (2006.01) |
| *A61K 31/444* | (2006.01) |
| *C07D 401/14* | (2006.01) |

(52) U.S. Cl.
CPC .............. *C07D 471/04* (2013.01); *A61P 9/10* (2018.01); *C07D 209/12* (2013.01); *C07D 209/14* (2013.01); *C07D 401/04* (2013.01); *C07D 401/14* (2013.01)

(58) Field of Classification Search
None
See application file for complete search history.

(56) References Cited

U.S. PATENT DOCUMENTS

| | | |
|---|---|---|
| 2005/0282821 A1 | 12/2005 | Lesur et al. |
| 2007/0293516 A1 | 12/2007 | Knight et al. |
| 2010/0272711 A1 | 10/2010 | Feldman et al. |
| 2012/0202785 A1 | 8/2012 | Heald et al. |

OTHER PUBLICATIONS

Edelstein, L., et al., "Racial difference in human platelet PAR4 reactivity reflects expression of PCTP and miR-376c," Nat Med 19:1609-16, 2013 (DOI 10.1038/nm.3385; PMID: 24216752).
Edelstein, L., et al., "Common variants in the human platelet PAR4 thrombin receptor alter platelet function and differ by race," Blood 124:3450-8, 2014.
Tourdot, B., et al., "Mechanism of race-dependent platelet activation through the protease-activated receptor-4 and Gq signaling axis," Arterioscler Thromb Vasc Biol 34:2644-50, 2014.
Wen, W., et al., "Substituted indoles as selective protease activated receptor 4 (PAR-4) antagonists: Discovery and SAR of ML354" Bioorg Med Chem Lett. Oct. 1, 2014;24(19):4708-13.
Young, Summer E., et al. "A Novel and Selective PAR4 Antagonist: ML354" Probe Reports from the NIH Molecular Libraries Program: NCBI Bookshelf (http://www.ncbi.njm.nih.gov/books/NBK280043/?report=printable), (received Apr. 15, 2013).

*Primary Examiner* — Zinna Northington Davis
(74) *Attorney, Agent, or Firm* — Riverside Law LLP

(57) ABSTRACT

A substance of Formula (I) for use as a medicament for the treatment of cardiovascular diseases, wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyl oxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkyl-methanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; and $R^4$ is selected from the group consisting of a hydrogen, a cyano, a $C_1$-$C_3$ sulfonyl, a nitro, and a trifluoromethyl.

(I)

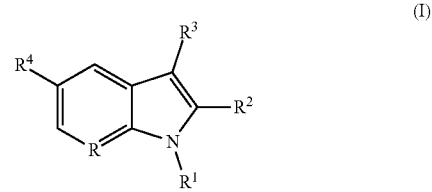

12 Claims, 9 Drawing Sheets

NON-SELECTIVE PROTEASE ACTIVATED RECEPTOR 4 ALA120THR ISOFORM ANTAGONIST

CROSS REFERENCE TO RELATED APPLICATIONS

This application is a National Phase under 35 U.S.C. 371 of International Application No. PCT/US16/57169, filed Oct. 14, 2016, which claims the benefit of provisional application 62/242,114, filed Oct. 15, 2015, the contents of which are herein incorporated by reference.

GOVERNMENT SUPPORT CLAUSE

This invention was made with government support under HL102482 awarded by the National Institutes of Health. The government has certain rights in the invention.

FIELD OF INVENTION

The present application is generally related to compounds, pharmaceutical compositions and methods of treatment using such pharmaceutical compositions for cardiovascular diseases that are not isoform preferential with regard to protease activated receptor 4 (PAR4) at the Ala120Thr isoform.

BACKGROUND OF INVENTION

Heart disease is a leading cause of death for men and women of all racial and ethnic backgrounds. Every year, approximately 1.2 million people will have a heart attack, while a further 500,000 individuals suffer from strokes. However, modern medicine has identified several therapeutic treatments to deal with the accumulation of platelets that are indicative of these diseases.

Anti-platelet therapies are commonly used in patients and tend to include aspirin, P2Y12 antagonists (e.g., Plavix [clopidogrel]) and the PAR1 antagonist vorapaxar. PAR4 is implicated with regard to treating certain cardiovascular diseases including thrombosis, coronary artery disease, cerebrovascular disease and neurological or pulmonary diseases that are mediated through the activation of thombin on the PAR4 receptor. PAR4, variance is highly conserved among generic populations and the Ala120Thr variant is very common in the population, with black subjects having a high allele frequency of Thr120, while whites have a high frequency of Ala120. Unfortunately, most patients treated with current anti-platelet therapies have recurrent vascular events and better treatments are needed.

Indeed, the "gold standard" and FDA-approved anti-platelet drugs are not as effective at inhibiting in vitro platelet aggregation from individuals expressing PAR4 Thr 120. Furthermore, anti-platelet therapies such as clopidogrel (PLAVIX®) are selective towards inhibiting platelet aggregation for individuals expressing PAR4 Ala120 but are not effective with regard to individuals expressing PAR4 Thr120. The limits of these therapies provide that patients should be tested to determine their genetic profile before they begin a treatment, so as to determine whether the treatment is likely to have any efficacy. For those who have the PAR4 Thr120 isoform, they are further burdened by lack of efficacy and options for treatment, thus disproportionally hurting a portion of the population over the other.

It has been previously disclosed that the compound YD-3 has been known to be a PAR4 antagonist, effective for the PAR4 Ala120 isoform and in human blood platelets stimulated with thrombin peptides that specifically activate PAR4. However, the PAR4 Thr120 isoform was relatively resistant to YD-3 inhibition, as well as all other commonly used anti-platelet drugs. Therefore individuals expressing the PAR4 Thr120 isoform do not receive optimal anti-platelet therapy compared to individuals who express only the Ala120 isoform. This has resulted in a discrepancy in the effectiveness of current therapies, based on the isoform of the PAR4 gene of the patient.

Therefore, new therapeutic compounds and compositions are necessary to provide universal treatment to patients, regardless of the PAR4 120 isoform. Specifically, such compounds and pharmaceutical compositions containing said compounds can be further utilized in methods of treatment that do not depend on the isoform of the PAR4 receptor for efficacy.

SUMMARY OF INVENTION

The present invention consists of compounds that antagonize PAR4 receptors regardless of which isoform is expressed. These compounds may be suitably administered to a mammal to reduce the risk of PAR4-induced platelet activation regardless of the isoform of the PAR4 receptor in the patient.

One embodiment of the present invention includes a substance of Formula I

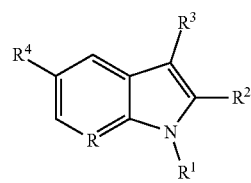

I for use as a medicament, wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; and $R^4$ is selected from the group consisting of a hydrogen, a cyano, a $C_1$-$C_3$ sulfonyl, a nitro, and a trifluoromethyl.

Another embodiment includes a substance of Formula I

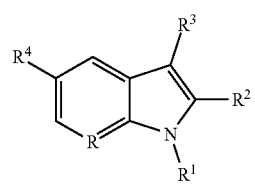

I for use as a medicament, wherein R is carbon; $R^1$ is a methyl; $R^2$ is a methyl alcohol or a $C_1$-$C_3$ N-alkylmethanamine; $R^3$ is a phenyl; and $R^4$ is a nitro.

Another embodiment includes a substance of Formula I

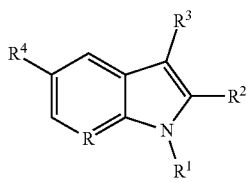

for use in treating a cardiovascular disease wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; and $R^4$ is selected from the group consisting of a hydrogen, a cyano, a $C_1$-$C_3$ sulfonyl, a nitro, and a trifluoromethyl.

Another embodiment includes a substance of Formula I

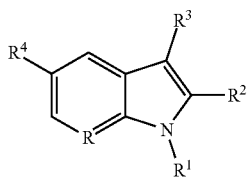

for use in treating a cardiovascular disease wherein R is carbon; $R^1$ is a methyl; $R^2$ is a methyl alcohol or a $C_1$-$C_3$ N-alkylmethanamine; $R^3$ is a phenyl; and $R^4$ is a nitro.

A Another embodiment includes a substance of Formula I

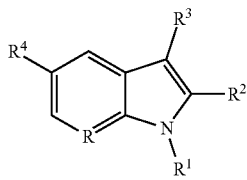

for use in treating a cardiovascular disease wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; and $R^4$ is selected from the group consisting of a hydrogen, a cyano, a $C_1$-$C_3$ sulfonyl, a nitro, and a trifluoromethyl.

Another embodiment includes a substance of Formula I

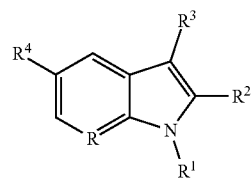

for use in treating a cardiovascular disease wherein R is carbon; $R^1$ is a methyl; $R^2$ is a methyl alcohol or a $C_1$-$C_3$ N-alkylmethanamine; $R^3$ is a phenyl; and $R^4$ is a nitro.

Another embodiment includes a substance of Formula I

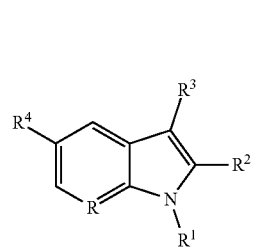

for use in treating a cardiovascular disease wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; and $R^4$ is selected from the group consisting of a hydrogen, a cyano, a $C_1$-$C_3$ sulfonyl, a nitro, and a trifluoromethyl, wherein the cardiovascular disease includes a PAR4 isoform.

Another embodiment includes a substance of Formula I

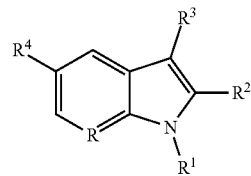

for use in treating a cardiovascular disease wherein R is carbon; $R^1$ is a methyl; $R^2$ is a methyl alcohol or a $C_1$-$C_3$ N-alkylmethanamine; $R^3$ is a phenyl; and $R^4$ is a nitro, wherein the cardiovascular disease includes a PAR4 isoform.

Another embodiment includes a substance of Formula I

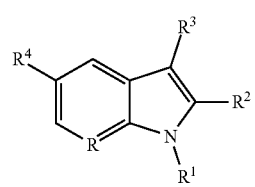

for use in treating a cardiovascular disease wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; and $R^4$ is selected from the group consisting of a hydrogen, a cyano, a $C_1$-$C_3$ sulfonyl, a nitro, and a trifluoromethyl, wherein the cardiovascular disease includes a PAR4 Ala120Thr isoform.

Another embodiment includes a substance of Formula I

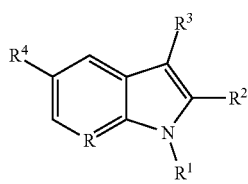

I for use in treating a cardiovascular disease wherein R is carbon; $R^1$ is a methyl; $R^2$ is a methyl alcohol or a $C_1$-$C_3$ N-alkylmethanamine; $R^3$ is a phenyl; and $R^4$ is a nitro, wherein the cardiovascular disease includes a PAR4 Ala120Thr isoform.

Another embodiment includes a substance of Formula I

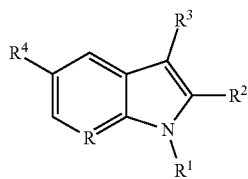

I for use in treating a cardiovascular disease wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; and $R^4$ is selected from the group consisting of a hydrogen, a cyano, a $C_1$-$C_3$ sulfonyl, a nitro, and a trifluoromethyl, wherein the cardiovascular disease includes a PAR4 isoform; testing a patient for the PAR4 isoform; and providing an effective dose of a substance of Formula I to the patient wherein the effective dose is modified based on the isoform of the patient.

Another embodiment includes a pharmaceutical composition for use in treating a cardiovascular diseases comprising a substance of Formula I:

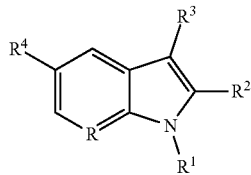

I wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; $R^4$ is selected from the group consisting of a hydrogen, a cyano, a $C_1$-$C_3$ sulfonyl, a nitro, and a trifluoromethyl; and a pharmaceutically acceptable carrier.

Another embodiment includes a substance of Formula I

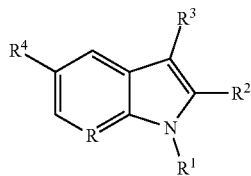

I for use in treating a cardiovascular disease wherein R is carbon; $R^1$ is a methyl; $R^2$ is a methyl alcohol or a $C_1$-$C_3$ N-alkylmethanamine; $R^3$ is a phenyl; and $R^4$ is a nitro.

Another embodiment includes a pharmaceutical composition for use in treating a cardiovascular diseases comprising a substance of Formula I:

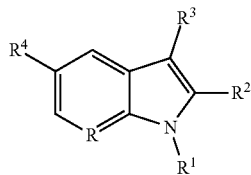

I wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; $R^4$ is selected from the group consisting of a hydrogen, a cyano, a $C_1$-$C_3$ sulfonyl, a nitro, and a trifluoromethyl; and a pharmaceutically acceptable carrier, wherein the cardiovascular disease comprises a PAR4 isoform.

Another embodiment includes a pharmaceutical composition for use in treating a cardiovascular diseases comprising a substance of Formula I:

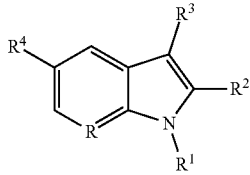

wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; $R^4$ is selected from the group consisting of a hydrogen, a cyano, a $C_1$-$C_3$ sulfonyl, a nitro, and a trifluoromethyl; and a pharmaceutically acceptable carrier, wherein the cardiovascular disease comprises a PAR4 Ala120Thr isoform.

Another embodiment includes a pharmaceutical composition for use in treating a cardiovascular diseases comprising a substance of Formula I:

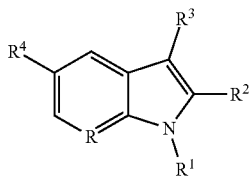

wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; $R^4$ is selected from the group consisting of a hydrogen, a cyano, a $C_1$-$C_3$ sulfonyl, a nitro, and a trifluoromethyl; and a pharmaceutically acceptable carrier, wherein the cardiovascular disease comprises a PAR4 isoform; testing a patient for the PAR4 isoform; and providing an effective dose of a substance of Formula I to the patient wherein the effective dose is modified based on the isoform of the patient.

Preferred compounds for antagonizing PAR 4 receptors include: A compound comprising the structure:

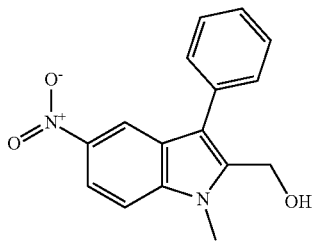 [SMILES: Cn1c(CO)c(-c2ccccc2)c2cc([N+](=O)[O-])ccc21]

A compound comprising the structure:

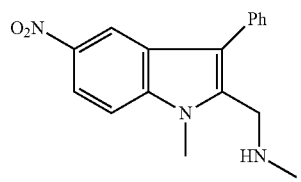 [SMILES: CNCc1c(-c2ccccc2)c2cc([N+](=O)[O-])ccc2n1C]

A compound comprising the structure:

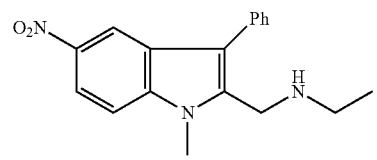 [SMILES: CCNCc1c(-c2ccccc2)c2cc([N+](=O)[O-])ccc2n1C]

A compound comprising the structure:

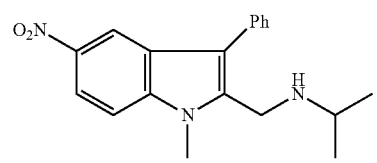

A further embodiment is directed to use of any of the compositions comprising Formula I for the manufacture of a medicament for the treatment of coronary heart disease or cardiovascular diseases.

In further embodiments, the compounds can be advantageously combined into a pharmaceutical composition that is suitable for administering to a mammal for the treatment of certain diseases such as thrombosis, coronary artery disease, cerebrovascular disease and neurologic or pulmonary disease. The compounds are mediated through the activation of the PAR4 receptor, and have the advantage of working just as effectively for individuals who may or may not possess the PAR4 Thr120 isoform. Accordingly, the compounds can be administered to a patient for treatment of cardiovascular diseases regardless of the PAR4 isoform at position 120.

Therefore, a further embodiment is directed to a method for treatment of cardiovascular diseases comprising administering to a patient an effective amount of a PAR4 antagonist according to Formula I that is effective at antagonizing PAR4 regardless of the isoform at position 120.

Therefore, a further embodiment is directed to a method of treating a patient suffering from a cardiovascular disease, wherein said patient is tested to have isoform PAR4 Thr120, and wherein the patient is administered an effective amount of Formula I.

A further embodiment is directed towards a method of treatment of a patient having cardiovascular disease, comprising a first step of determining the mutation of the patient at position 120; determining a dose of a composition comprising Formula I based upon the mutation of the patient at position 120; administering to the patient the determined dose of composition comprising Formula I.

A further embodiment comprises a method of treatment or use of a composition for treating a patient suffering from coronary heart disease or cardiovascular disease wherein the composition comprises an active ingredient selected from the group consisting of Compositions 1-44 and combinations thereof. In certain embodiments, the method comprises a first step of deterring the mutation of the patient suffering from coronary heart disease at position 120, and determining an appropriate dose of the composition based upon the determined mutation.

A method of treatment of a patient having cardiovascular disease comprising: determining the mutation of the patient at position 120; determining a dose of a composition comprising Formula I:

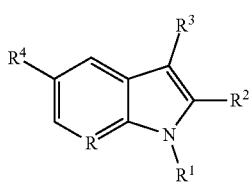

I wherein R is nitrogen or carbon;
$R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl;
$R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and
$R^3$ is a phenyl or a methoxypyridinyl;
$R^4$ is selected from the group consisting of a hydrogen, a cyano, a $C_1$-$C_3$ sulfonyl, a nitro, and a trifluoromethyl; and a pharmaceutically acceptable carrier; wherein the dose is based upon the mutation of the patient at position 120; administering to the patient the determined dose of composition comprising Formula I.

DETAILED DESCRIPTION OF THE DRAWINGS

Figure 1:
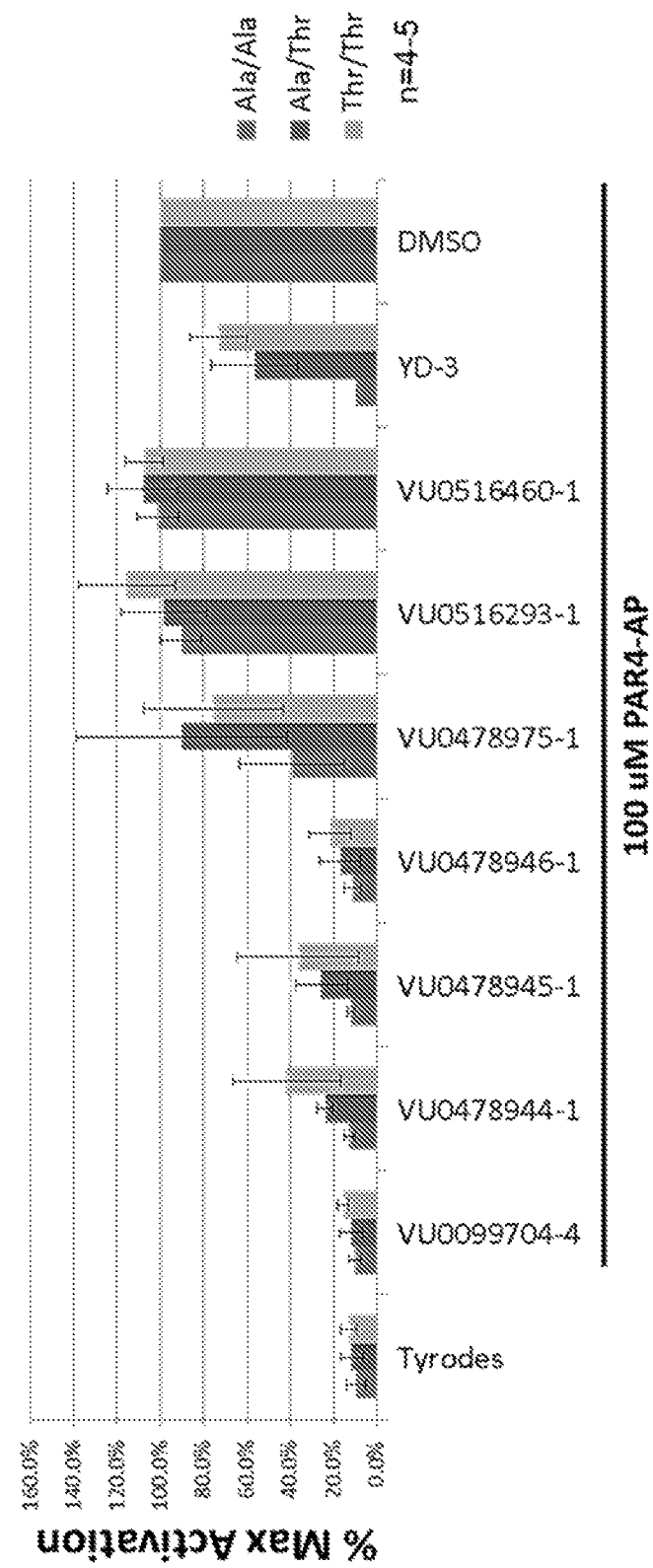
FIG. 1. Depicts a summary of results using all three PAR4 variants.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 5% of the numerical value of the number with which it is being used. Therefore, about 50% means in the range of 45%-55%.

"Administering" when used in conjunction with a therapeutic means to administer a therapeutic directly to a subject, whereby the agent positively impacts the target. "Administering" a composition may be accomplished by, for example, injection, oral administration, topical administration, or by these methods in combination with other known techniques. Such combination techniques include heating, radiation, ultrasound and the use of delivery agents. When a compound is provided in combination with one or more other active agents (e.g. other anti-atherosclerotic agents such as the class of statins), "administration" and its variants are each understood to include concurrent and sequential provision of the compound or salt and other agents.

By "pharmaceutically acceptable" it is meant the carrier, diluent, adjuvant, or excipient must be compatible with the other ingredients of the formulation and not deleterious to the recipient thereof.

"Composition" as used herein is intended to encompass a product comprising the specified ingredients in the specified amounts, as well as any product which results, directly or indirectly, from combination of the specified ingredients in the specified amounts. Such term in relation to "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound to the present invention and a pharmaceutically acceptable carrier.

As used herein, the term "agent," "active agent," "therapeutic agent," or "therapeutic" means a compound or composition utilized to treat, combat, ameliorate, prevent or improve an unwanted condition or disease of a patient. Furthermore, the term "agent," "active agent," "therapeutic agent," or "therapeutic" encompasses a combination of one or more of the compounds of the present invention.

A "therapeutically effective amount" or "effective amount" of a composition is a predetermined amount calculated to achieve the desired effect, i.e., to inhibit, block, or reverse the activation, migration, proliferation, alteration of cellular function, and to preserve the normal function of cells. The activity contemplated by the methods described herein includes both medical therapeutic and/or prophylactic treatment, as appropriate, and the compositions of the invention may be used to provide improvement in any of the conditions described. It is also contemplated that the compositions described herein may be administered to healthy subjects or individuals not exhibiting symptoms but who may be at risk of developing a particular disorder. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the chosen dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refer to both therapeutic treatment and prophylactic or preventative measures, wherein the object is to prevent or slow down (lessen) an undesired physiological condition, disorder, or disease, or to obtain beneficial or desired clinical results. For the purposes of this invention, beneficial or desired results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes prolonging survival as compared to expected survival if not receiving treatment.

Heart disease and other diseases related to accumulation of platelets in the blood affect millions of people each year. While some therapies have proven to be effective, their effectiveness is limited in certain patient populations, which have now been identified as having a variation in the PAR 4 gene. PAR4 120 is susceptible to both the Thr and Ala isoform wherein current therapies are effective for the alanine version of the PAR4 gene.

Among the embodiments provided herein include certain compounds based upon Formula I, pharmaceutical compositions, and methods of use of the same in the treatment of persons suffering from heart disease or another platelet aggregation disease through the administration of compounds or pharmaceutical compositions to the patient irrespective of the isoform of the PAR4 gene.

Formula I is generally defined by the following structure:

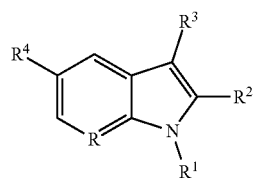

wherein R is nitrogen or carbon; $R^1$ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl; $R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; and $R^4$ is selected from the group consisting of a hydrogen, a cyano, a $C_1$-$C_3$ sulfonyl, a nitro, and a trifluoromethyl. Formula I, can be then formulated into an appropriate composition and/or medicament for use in treatment or provided in certain methods of treatment so as to treat a patient. Specific Compounds are depicted herein that are particularly suited for formulation.

An anti-platelet therapy is presented that effectively antagonizes both the PAR4 Thr120 and Ala120 isoforms through use of methods of treatment that provide for non-specific antagonism with regard to PAR, thus providing more effective anti-thrombotic treatments for all patients. The non-specific antagonism will also provide for a much more effective treatment for the patients that express 120Thr isoform.

PAR4 gene-Myocardial infarction and other ischemic arterial diseases like stroke typically result from an occlusive platelet thrombus formed at the site of a ruptured atherosclerotic plaque. Thrombin is an especially potent physiologic agonist mediating in vivo platelet activation, and human platelets express two thrombin receptors, protease activated receptors 1 and 4, referred to as PAR1 and PAR4, both of which mediate thrombin signaling in platelet activation. During thrombin-induced platelet activation these receptors couple to specific G proteins, leading to activation of phospholipases and protein kinases, hydrolysis of phosphoinositides and increased cytoplasmic calcium. Numerous differences in platelet activation have been characterized following stimulation of PAR1 or PAR4. For example, compared to PAR1, PAR4 induces a more sustained rise in intracellular calcium and is responsible for the majority of intracellular calcium flux. These observations suggest different kinetics or signaling pathways through platelet PAR1 and PAR4.

A common variant (polymorphism; SNP rs773902) in F2RL3 (The gene encoding PAR4 protein) that results in an Ala-Thr dimorphism at residue 120 in PAR4. White individuals have a high frequency of Ala120, blacks have a high frequency of Thr120, and PAR4 Thr120 is associated with greater platelet reactivity ($p=9.15 \times 10^{-16}$) after accounting for race, age and sex in response to the PAR4-activating peptide (PAR4-AP), AYPGKF. When over-expressed in HEK 293 cells and stimulated them with PAR4-AP, greater cell activation was observed for the Thr120 variant than the Ala120 variant.

The Ala120Thr variant is located in the second exon of F2RL3 and alters residue 120 in the second transmembrane domain of PAR4. The "G" allele of rs773902 encodes alanine (Ala) and the "A" allele encodes threonine (Thr). The F2RL3 gene and variants are located on human chromosome 19 and are inherited in a Mendelian fashion. The allele frequency of rs773902 is significantly different between blacks and whites (p $4.31 \times 10^{-16}$). The rs773902 "A" allele (Thr120) is most prominent in subjects of sub-Saharan African and Papua New Guinea ancestry, whereas the "G" allele (Ala120) predominates in subjects from Europe, Asia and the Americas.

Accordingly, compounds that antagonize PAR4 irrespective of the isoform provide for novel therapeutic strategies to treat those suffering from cardiovascular diseases and other diseases related to platelet aggregation. By antagonizing the PAR4 receptor, the compounds described herein are effective at inhibiting platelet aggregation and thus provide for efficacy of such compounds for the treatment of these diseases.

Each of the compounds 1-44 based upon Formula I utilize an indole or azaindole core with functional groups added thereto. The compositions were placed under the protocols described herein and tested for efficacy in blocking PAR4-induced platelet activation in the samples. It is particular noted that four compounds, VU0099704-4, VU0478944-1, VU0478045-1 and VU478046-1 provided for the greatest effective blockade of PAR4-induced platelet activation for subjects regardless of the isoform variant present on the PAR4 receptor as depicted in FIG. 1.

FIG. 1. Summary of results using all three PAR4 variants. Based on the initial screen (FIGS. 2-9 and other data not shown), platelets from 4 or 5 subjects of each of the 3 genotypes indicated as Ala/Ala or Ala/Thr or Thr/Thr were studied for the ability of the 5 lead compounds (VU0099704-4, VU0478944-1, VU0478945-1, VU0478946-1 and VU0478975-1), 2 negative control compounds (VU0516293-1, VU0516460-1), YD-3 and a vehicle control (DMSO) to inhibit PAR4-included platelet activation. Tyrodes indicates buffer used instead of PAR4-AP and shows no platelet activation. Data are shown as the average of the percent of maximal activation, where maximal activation was the DMSO data.

Figure 2:
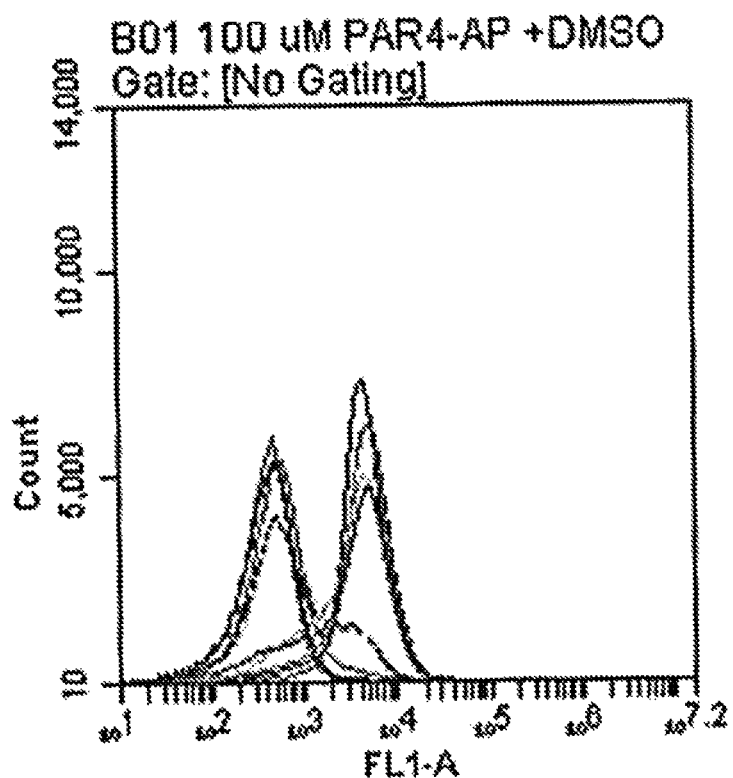
FIG. 2. Depicts a screening assay on first set of 8 compounds.
Figure 2:
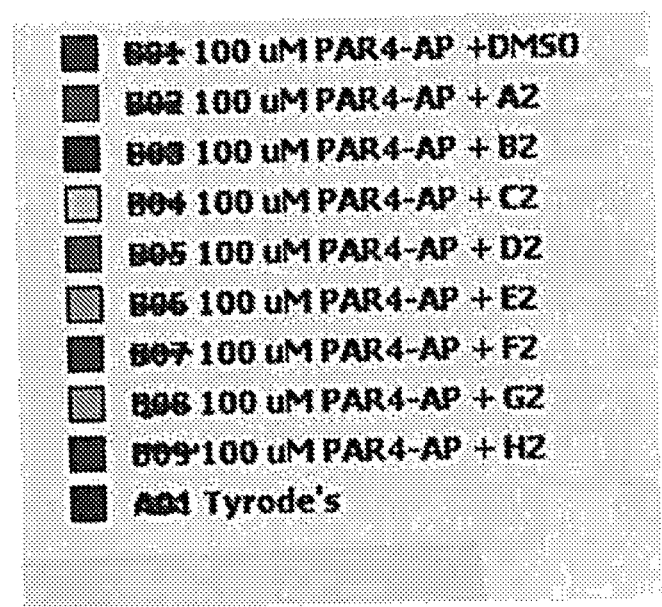

FIG. 2. Screening assay on first set of 8 compounds. Flow cytometry data in left panel. Legend is on right. A2 refers to compound VU0099704-4; B2 refers to compound VU0478944-1; C2 refers to compound VU0478945-1; D2 refers to compound VU0478946-1; E2 refers to compound VU0478975-1. F2, G2 and H2 refer to additional compounds that had no effect on PAR4-mediated platelet activation.

Figure 3:
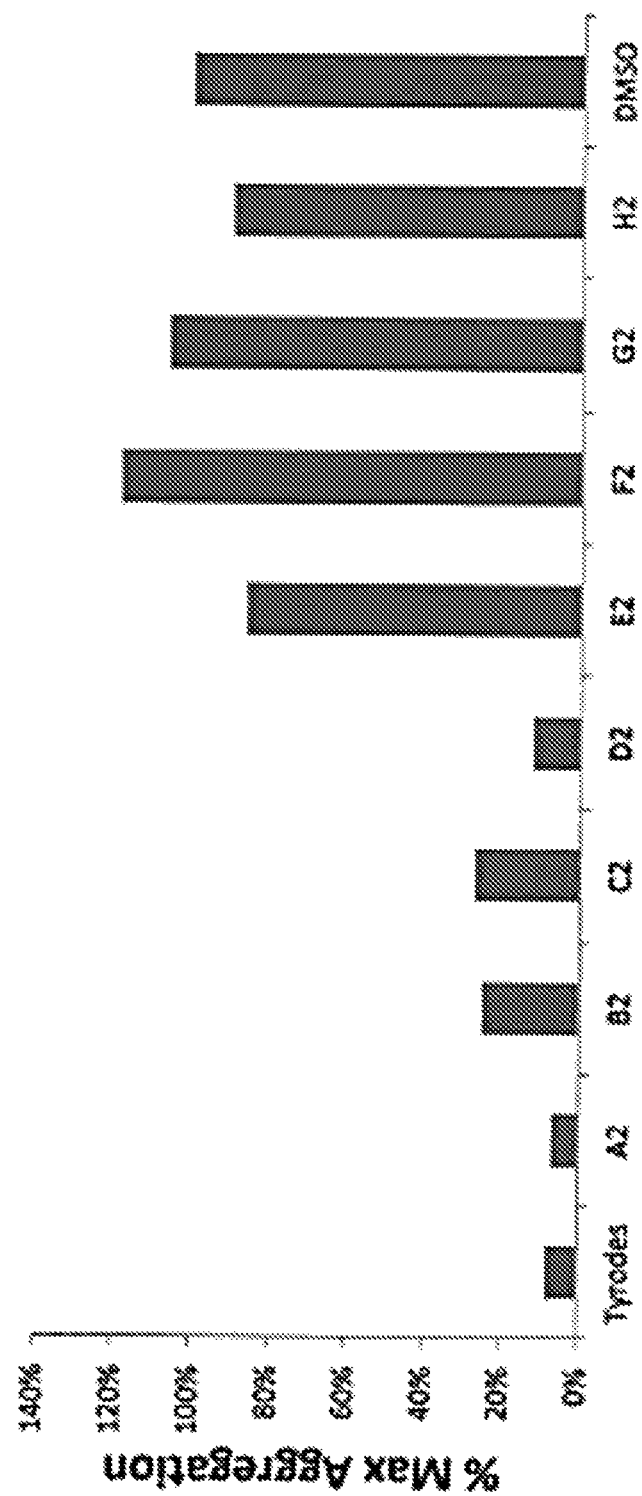
FIG. 3. Depicts a bar plot of flow cytometry data shown in FIG. 2.

FIG. 3. Bar plot of flow cytometry data shown in FIG. 2. Data are shown as percent of maximal activation, where maximal activation was the DMSO data.

Figure 4:
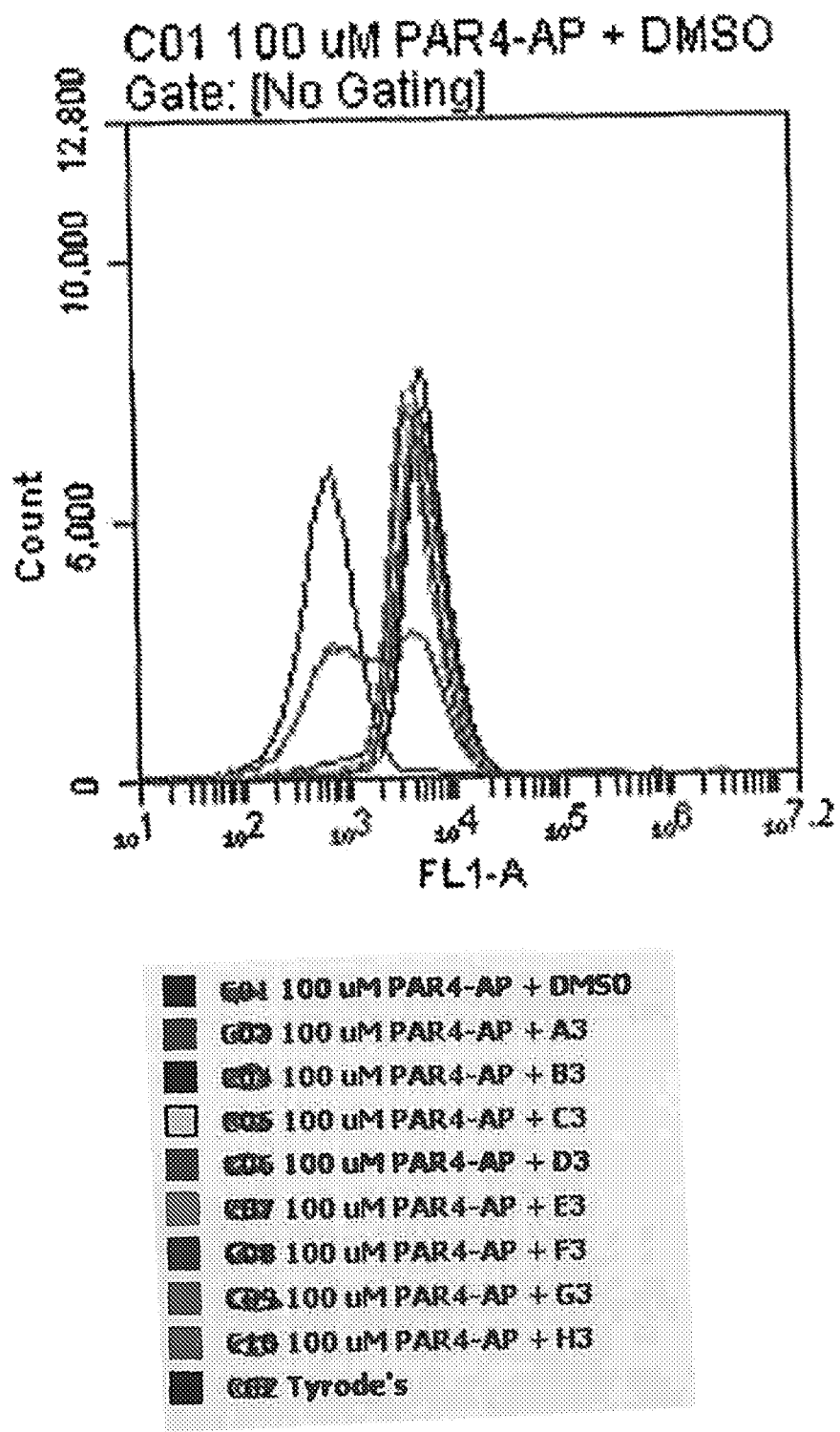
FIG. 4. Depicts a screening assay on second set of 8 compounds.

FIG. 4. Screening assay on second set of 8 compounds. Flow cytometry data in left panel. Legend is on right. A3, B3, C3, D3, E3, F3, G3 and H3 refer to additional compounds that had no effect on PAR4-mediated platelet activation.

Figure 5:
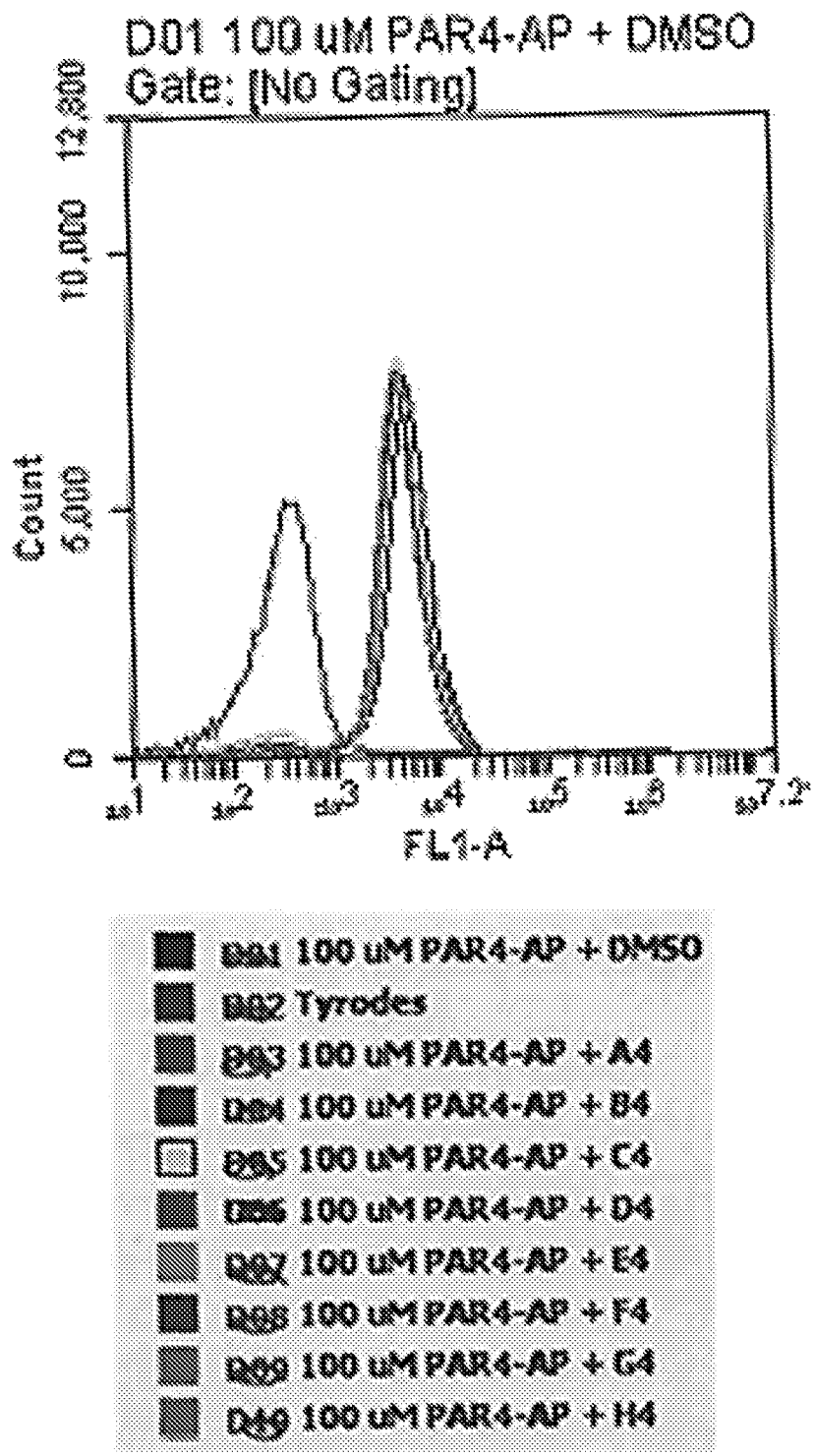
FIG. 5. Depicts a screening assay on third set of 8 compounds.

FIG. 5. Screening assay on third set of 8 compounds. Flow cytometry data in left panel. Legend is on right. A4, B4, C4, D4, E4, F4, G4 and H4 refer to additional compounds that had no effect on PAR4-mediated platelet activation.

Figure 6:
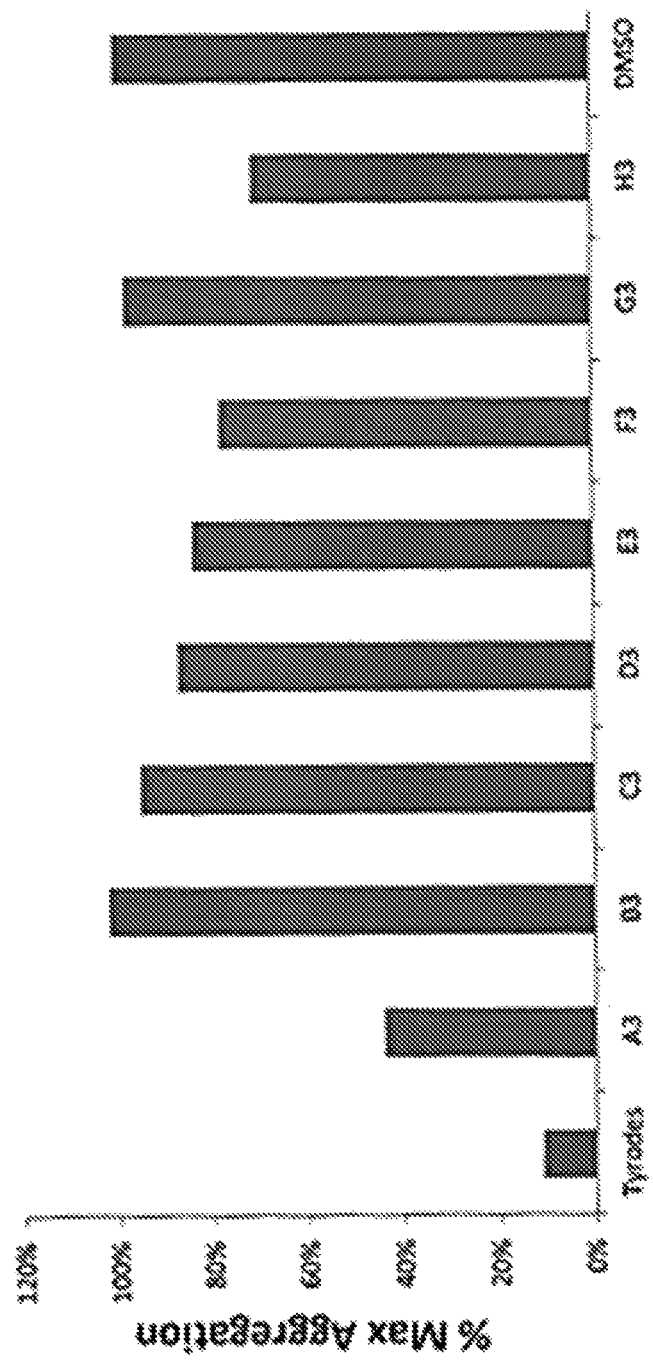
FIG. 6. Depicts a bar plot of flow cytometry data shown in FIG. 4.

FIG. 6. Bar plot of flow cytometry data shown in FIG. 4. Data are shown as percent of maximal activation, where maximal activation was the DMSO data.

Figure 7:
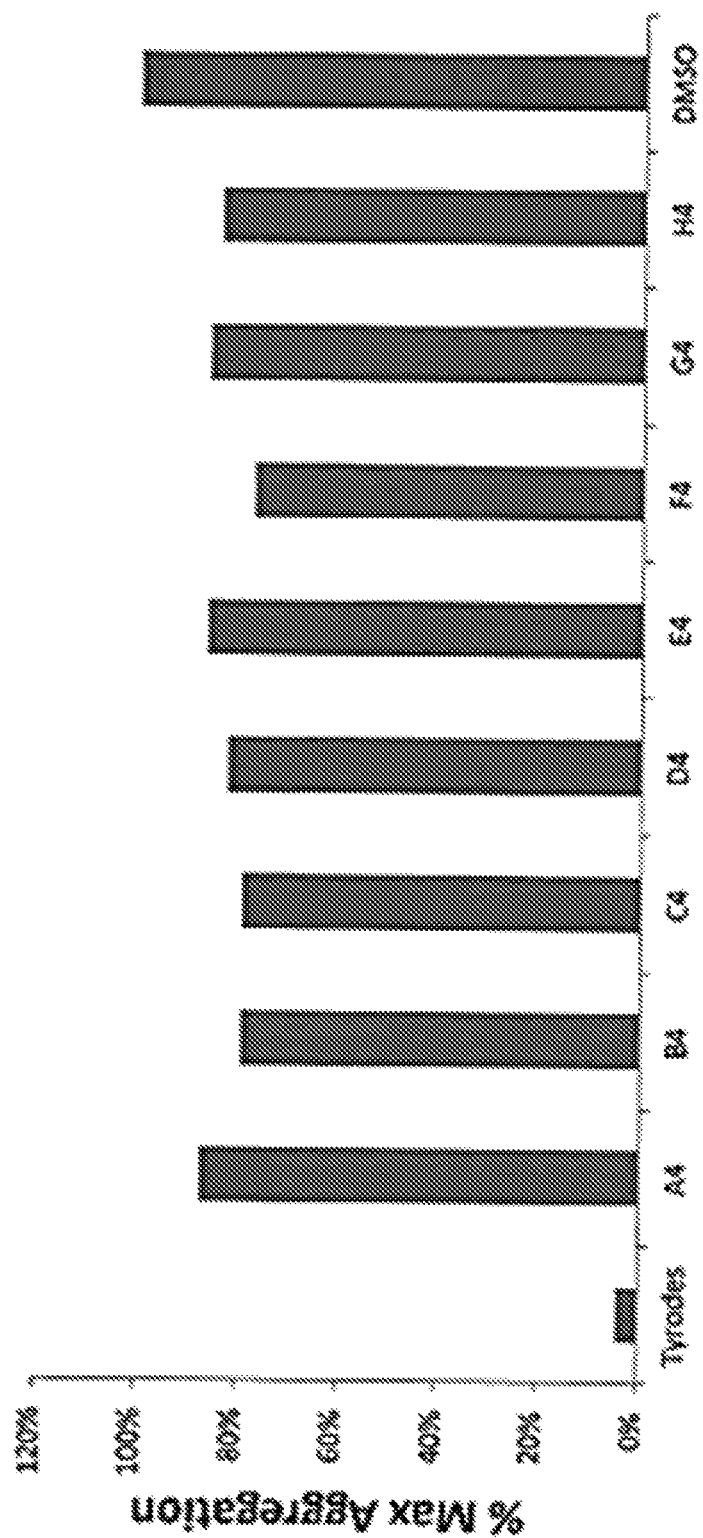
FIG. 7. Depicts a bar plot of flow cytometry data shown in FIG. 5.

FIG. 7. Bar plot of flow cytometry data shown in FIG. 5. Data are shown as percent of maximal activation, where maximal activation was the DMSO data.

Figure 8:
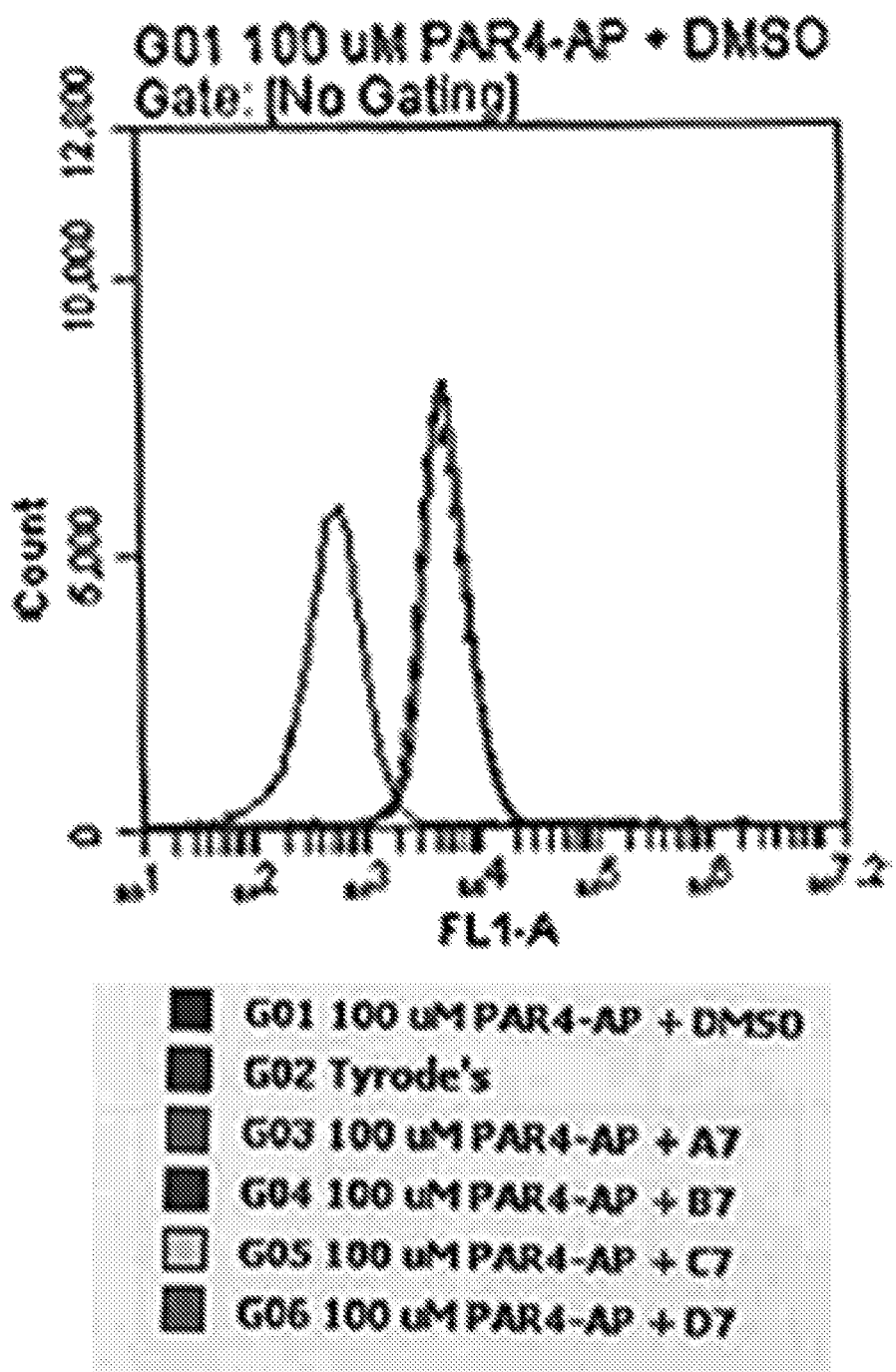
FIG. 8. Depicts a screening assay on fourth set of 4 compounds.

FIG. 8. Screening assay on fourth set of 4 compounds. Flow cytometry data in left panel. Legend is on right. A7, B7, C7, D7 refer to additional compounds that had no effect on PAR4-mediated platelet activation.

Figure 9:
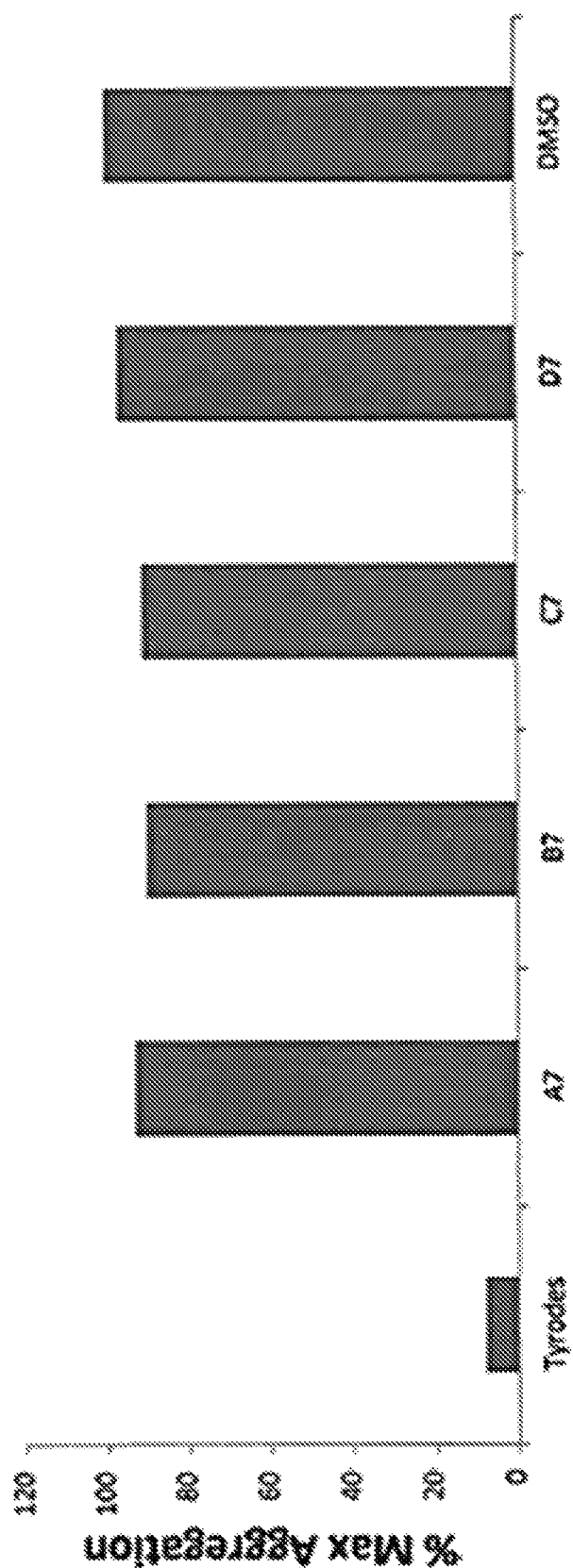
FIG. 9. Depicts a bar plot of flow cytometry data shown in FIG. 8.

FIG. 9. Bar plot of flow cytometry data shown in FIG. 8. Data are shown as percent of maximal activation, where maximal activation was the DMSO data.

Therefore, these compositions may be advantageously utilized to block PAR4-induced platelet accumulation for patents regardless of the isoform variation of the PAR4 receptor in the patient.

The compounds identified herein are suitable for being administered in a pharmaceutical composition as known to one of ordinary skill in the art. For example, the compositions can be ingested orally in the form of a solid pill or a liquid formulation. Furthermore, the compositions can be provided in a pharmaceutical composition that is suitably isotonic for immediate administration subcutaneously or through IV or direct administration to a vein or artery.

The term "pharmaceutically-acceptable salts" embraces salts commonly used to form alkali metal salts and to form additional salts of free acids or free bases. The nature of the salt is not critical, provided that it is pharmaceutically-acceptable. Suitable pharmaceutically-acceptable acid addition salts of compounds of Formula I may prepared from an inorganic acid or from an organic acid. Examples of such inorganic acids are hydrochloric, hydrobromic, hydroiodic, nitric, carbonic, sulfuric and phosphoric acid. Appropriate organic acids may include aliphatic, cycloaliphatic, aromatic, araliphatic, heterocyclic, carboxylic and sulfonic classes of organic acids. Examples of such organic acids include formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydroxybenzoic, phylacetic, mandelic, embonic, methanesulfonic, ethanesulfonic, benzenesulfonic, pantothenic, 2-hydroxyethanesulfonic, toluenesulfonic, sulfanilic, cyclohyexylaminosuflonic, stearic, algenic, 3-hydrobutyric, galactaric and galacturnoic acid. Suitable pharmaceutically-acceptable base addition salts of compounds of Formula I include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, triethylamine, trimethylamine. All the listed salts of the corresponding compound of the invention may be prepared by conventional means known to one of ordinary skill in the art. One example of a conventional method of salt formation is by reacting the appropriate acid or base with the compounds of Formula I at various mole ratios. Another method is by using different mole ratios of the appropriate acid or base in various solvent systems to control the concentration of the dissociated species of the compounds of Formula I to maximize salt formation. The present invention also contemplates crystalline forms of the salts described herein.

Crystalline forms of the compounds of Formula I, may also include but are not limited to hydrates, solvates, and co-crystals. Crystalline solvates include solvents including but not limited to the following: MeOH, EtOH, AcOH, EtOEt, AcOEt, acetone, DMSO, DMF, MeCN, $CH_2Cl_2$, $CHCl_3$, $CCl_4$, dioxane, THF, benzene, toluene, p-xylene, and hexane.

Crystalline hydrates and solvates may be stoichiometric as according to the mole ratio of the water or organic solvent molecule to the compound or salt thereof. The crystalline hydrate may also be non-stoichiometric depending on the conditions of the unit cell which result in a thermodynamically or kinetically stable crystal. Crystalline salts and co-crystals may also be stoichiometric or non-stoichiometric for reasons stated above. One of skill in the art of crystallography understands that the components in the unit cell of a crystal may or may not be stoichiometric depending on the conditions which stabilize the crystal.

Administration and Compositions

The compounds of Formula I can be administered to a patient in certain methods of treatment of cardiovascular diseases, wherein the method is directed to administering to a patient a sufficient amount of a compound according to Formula I. Efficacy of these compounds is indicated based upon the results provided herein, which have a direct correlation to the human receptor. (Blood, 2014 Nov. 27; 124(23): 3450-3458). Accordingly, the ability to treat patients with chronic heart disease despite the prevalence of racial disparity in prior existing drugs, based upon the methods of treatment as described herein.

The compounds and pharmaceutically-acceptable salts thereof can be administered by means that produces contact of the active agent with the agent's site of action. They can be administered by conventional means available for use in conjunction with pharmaceuticals in a dosage range of 0.001 to 1000 mg/kg of mammal (e.g. human) body weight per day in a single dose or in divided doses. One dosage range is 0.01 to 500 mg/kg body weight per day orally in a single dose or in divided doses. Administration can be delivered as individual therapeutic agents or in a combination of therapeutic agents. They can be administered alone, but typically are administered with a pharmaceutically acceptable excipient selected on the basis of the chosen route of administration and standard pharmaceutical practice.

Compounds can be administered by one or more ways. For example, the following routes may be utilized: oral, parenteral (including subcutaneous injections, intravenous, intramuscular, intrasternal injection or infusion techniques), inhalation, buccal, sublingual, or rectal, in the form of a unit dosage of a pharmaceutical composition containing an effective amount of the compound and optionally in combination with one or more pharmaceutically-acceptable excipients such as stabilizers, anti-oxidants, lubricants, bulking agents, fillers, carriers, adjuvants, vehicles, diluents and other readily known excipients in standard pharmaceutical practice.

Liquid preparations suitable for oral administration (e.g. suspensions, syrups, elixirs and other similar liquids) can employ media such as water, glycols, oils, alcohols, and the like. Solid preparations suitable for oral administration (e.g. powders, pills, capsules and tablets) can employ solid excipients such as starches, sugars, kaolin, lubricants, binders, disintegrating agents, antioxidants and the like.

Parenteral compositions typically employ sterile water as a carrier and optionally other ingredients, such as solubility aids. Injectable solutions can be prepared, for example, using a carrier comprising a saline solution, a glucose solution or a solution containing a mixture of saline and glucose. Further guidance for methods suitable for use in preparing pharmaceutical compositions is provided in *Remington: The Science and Practice of Pharmacy*, 21$^{st}$ edition (Lippincott Williams & Wilkins, 2006).

Therapeutic compounds can be administered orally in a dosage range of about 0.001 to 1000 mg/kg of mammal (e.g. human) body weight per day in a single dose or in divided doses. One dosage range is about 0.01 to 500 mg/kg body weight per day orally in a single dose or in divided doses. For oral administration, the compositions can be provided in the form of tablets or capsules containing about 1.0 to 500 mg of the active ingredient, particularly about 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In view of the factors affecting the specific dose level and frequency it is contemplated that the dose frequency can range from multiple doses daily to monthly dosages. The preferred dose frequency ranges from twice a day to every two weeks. A more preferred dose frequency ranges from twice a day to weekly. A most preferred dose frequency ranges from twice a day to twice a week.

In the methods of various embodiments, pharmaceutical compositions including the active agent can be administered to a subject in an "effective amount." An effective amount may be any amount that provides a beneficial effect to the patient, and in particular embodiments, the effective amount is an amount that may 1) prevent the subject from experiencing one or more adverse effects associated with a administered agents, such as those used to diagnose, identify, and treat medical conditions, 2) reduce side effects experienced by the subject as a result of a medical therapy or reduce the side effects known to result from such therapies, and/or 3) eliminate side effects resulting from a medical treatment experienced by the subject prior to administration of the active agent or eliminate the side effects known to result from such treatment.

Pharmaceutical formulations containing the compounds of the invention and a suitable carrier can be in various forms including, but not limited to, solids, solutions, powders, fluid emulsions, fluid suspensions, semi-solids, and dry powders including an effective amount of an the active agent of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, Modern Pharmaceutics, Banker & Rhodes, Marcel Dekker, Inc. (1979); and *Goodman & Gilman's, The Pharmaceutical Basis of Therapeutics*, 6th Edition, MacMillan Publishing Co., New York (1980) both of which are hereby incorporated by reference in their entireties can be consulted.

Other embodiments of the invention include the active agent prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

In another exemplary embodiment, an oily preparation of an active agent prepared as described above may be lyophilized to form a solid that may be mixed with one or more pharmaceutically acceptable excipient, carrier or diluent to form a tablet, and in yet another embodiment, the active agent may be crystallized to from a solid which may be combined with a pharmaceutically acceptable excipient, carrier or diluent to form a tablet.

The means and methods for tableting are known in the art and one of ordinary skill in the art can refer to various references for guidance. For example, *Pharmaceutical Manufacturing Handbook: Production and Processes*, Shayne Cox Gad, John Wiley & Sons, Inc., Hoboken, N.J. (2008), which is hereby incorporated by reference in its entirety can be consulted.

Further embodiments which may be useful for oral administration of the active agent include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt. Other suitable diluents include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids may have between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil," refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, macrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko).

Polyethylene glycol: As used herein, the term "polyethylene glycol" or "PEG" refers to a polymer containing ethylene glycol monomer units of formula —O—CH$_2$—CH$_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to a monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may use in the synthesis as well. Suitable stearoyl macrogol glycerides include, but are not limited to, Gelucire® 50/13 (available from Gattefosse).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include the active agent administered in combination with other active such as, for example, adjuvants, protease inhibitors, or other compatible drugs or compounds where such combination is seen to be desirable or advantageous in achieving the desired effects of the methods described herein.

Other embodiments of the present invention include a pharmaceutical composition comprising an effective amount of the active agent and one or more pharmaceutically acceptable excipient. Other embodiments include a pharmaceutical composition comprising an effective amount of pharmaceutically-acceptable salts of the active agent. Other embodiments include a pharmaceutical composition comprising an effective amount of pharmaceutically-acceptable salts of active agent and a pharmaceutically-acceptable excipient.

In yet other embodiments, the active agent may be combined with one or more secondary agents.

The compositions as described herein are therefore suitable in methods of treatment of patients suffering from cardiovascular disease related to the accumulation of platelets in the blood. Of these, heart attacks and strokes are significant risk factors for those whom are obese or have other risk factors including high cholesterol or high blood pressure.

Treatment of these diseases can be mediated through reduction in the accumulation of these platelets which therefore prevents or reduces the risk for significant clotting or blockage in the body. PAR4 is a thrombin receptor on platelets, wherein PAR4 activation induces platelet activation and a platelet clot. Therefore, preventing the activation of PAR4 prevents the induction of a platelet clot and prevents or reduces the risk for disease attributed to the effects of these blockages.

Therefore a preferred embodiment is directed to a method for treatment of a patient having risk for accumulation of platelets in the blood or for platelet activation, wherein a pharmaceutical composition a compound of Formula I, is effective for treating coronary heart disease. Further embodiments comprising a method of treating a patient suffering from coronary heart disease with a composition comprising an active ingredient consisting of VU0099704-4, VU0478944-1, VU0478045-1, VU478046-1, and combinations thereof, wherein said composition is effective for treating and reducing the risk of platelet activation and blockage in said patient.

Materials and Methods

Compound Preparation:

Blood was drawn in 6 ACD yellow top tubes from subject TJU-47. Platelets were washed using the washed platelet protocol. Platelets were then rested at 37° C. for thirty minutes.

Forty four compounds synthesized from Formula I backbone were screened. Each 10 mm compound was thawed, voltexed, and spun at 1000 g for one minute. Each tube was labeled for each compound with an addition of 99 µl of Tyrodes.

1 mL of each compound was added to the corresponding tube, voltexed, and placed on ice. Final concentrations consisted of a stock of 100 µM.

Each of the tested compounds were diluted to a concentration of 5 m with a final concentration of 1% DMSO.

List of Compounds
Compound 1-VU0099704-4-
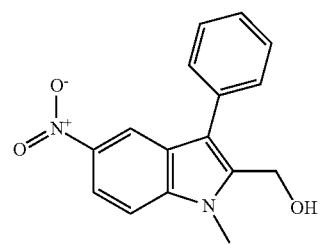
Compound 2-VU0478944-1
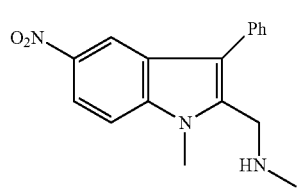
Compound 3-VU0478945-1
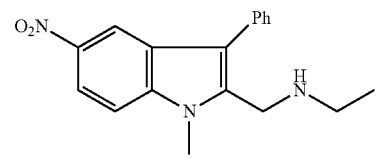
Compound 4-VU0478946-1
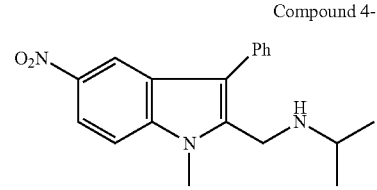
Compound 5-VU0478971-1
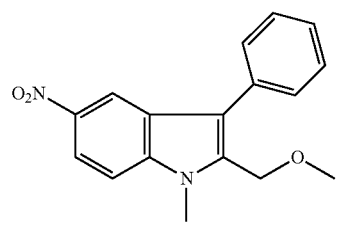
Compound 6-VU0478972-1
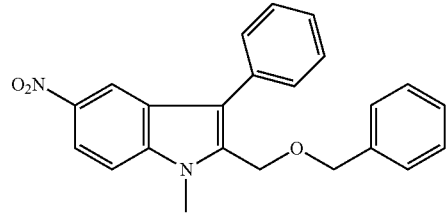
Compound 7-VU0478973-1
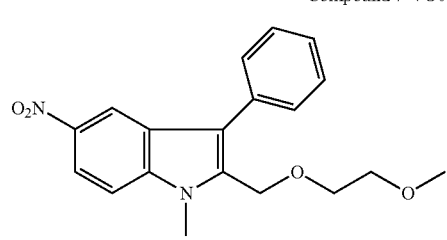
Compound 8-VU0478974-1
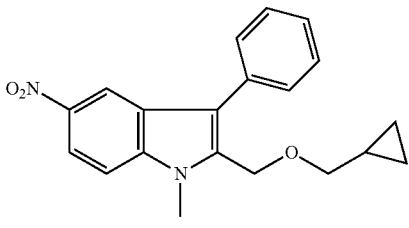
Compound 9-VU0478975-1
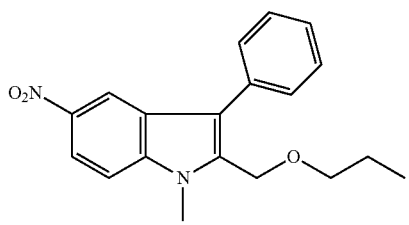
Compound 10-VU0478980-1
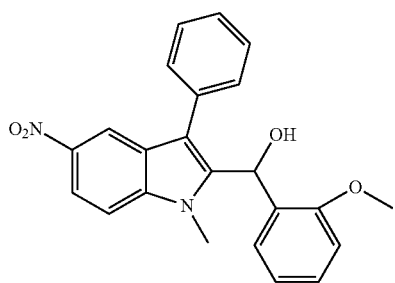
Compound 11-VU0516087-1
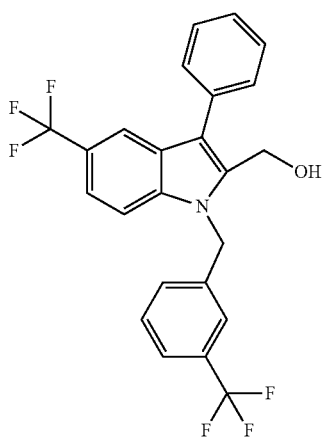
Compound 12-VU05160088-1

-continued
Compound 13-VU0516089-1
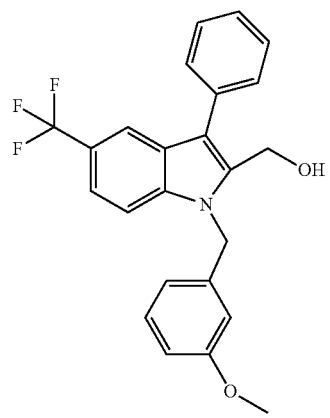
Compound 14-VU0516090-1
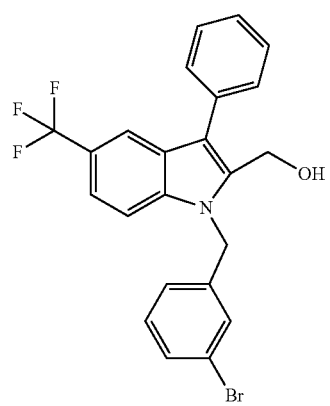
Compound 15-VU0516091-1
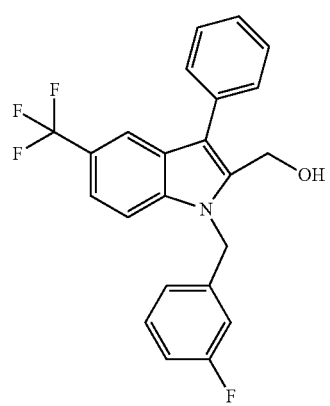
-continued
Compound 16-VU0516145-1
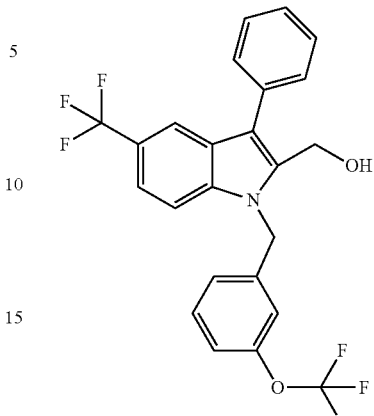
Compound 17-VU0516146-1
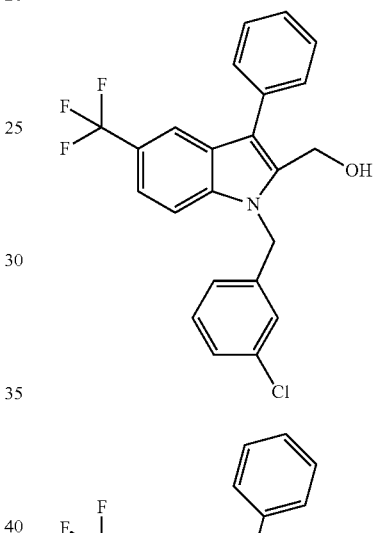
Compound 18-VU0516147-1
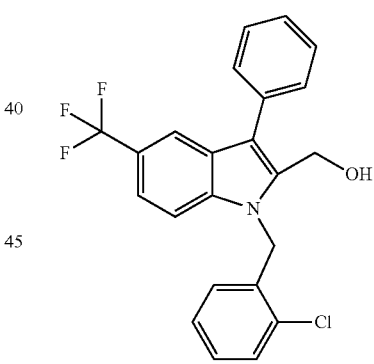
Compound 19-VU0516148-1
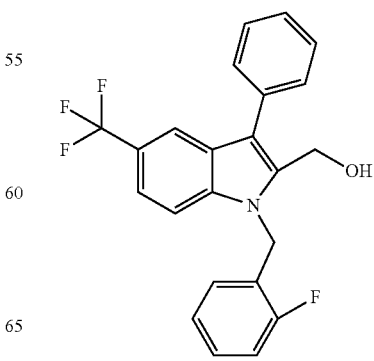

Compound 20-VU0516149-1
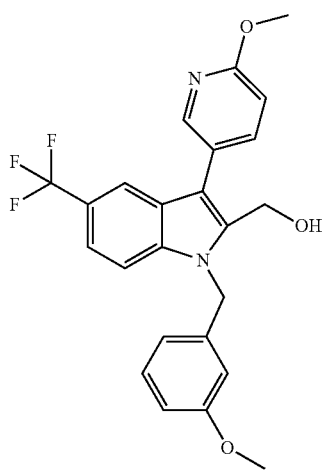
Compound 21-VU051612-1
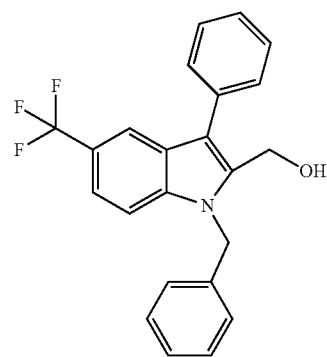
Compound 22-VU0516213-1
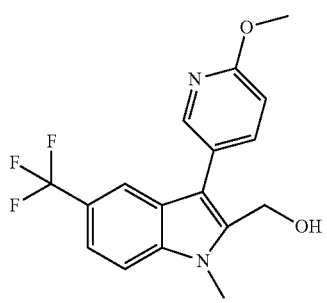
Compound 23-VU0516234-1
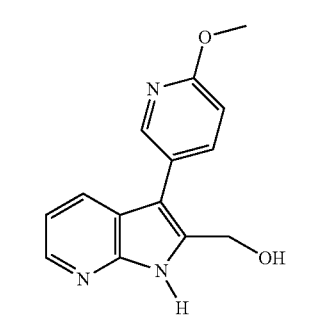
Compound 24-VU0516237-1
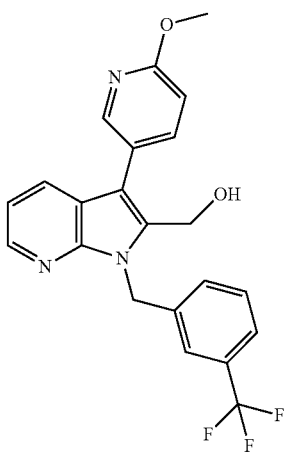
Compound 25-VU0516238-1
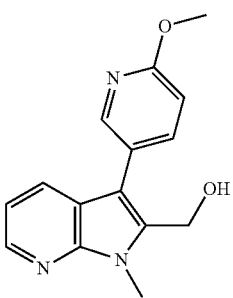
Compound 26-VU0516292-1
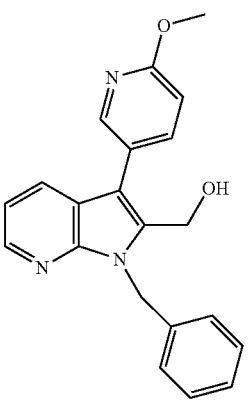
Compound 27-VU0516293-1
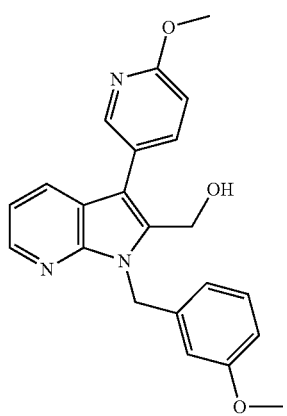

-continued
Compound 28-VU0516297-1
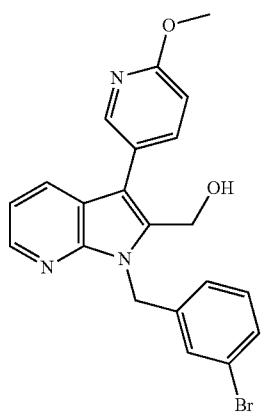
Compound 29-VU0516307-1
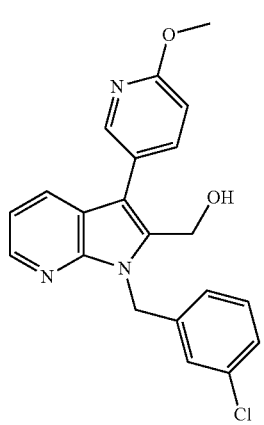
Compound 30-VU0516324-1
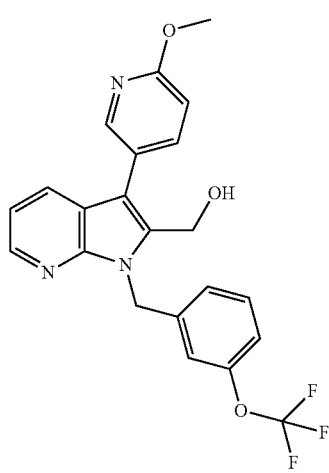
-continued
Compound 31-VU0516360-1
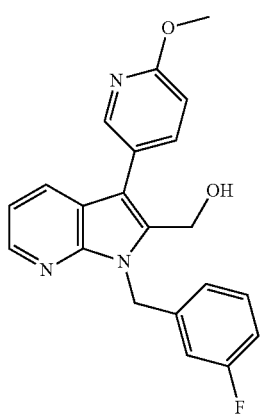
Compound 32-VU0516489-1
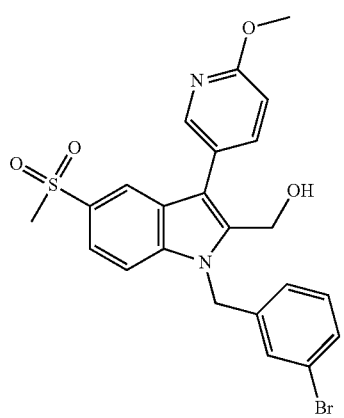
Compound 33-VU0516490-1
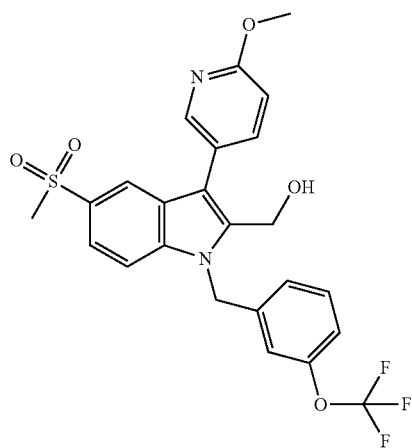

Compound 34-VU0516491-1
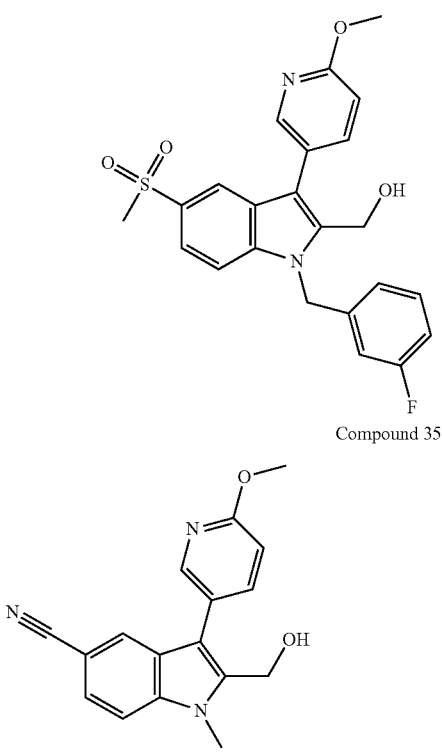
Compound 35-VU0516514-1
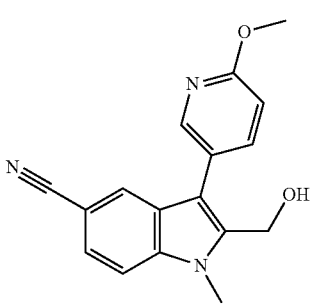
Compound 36-VU0516515-1
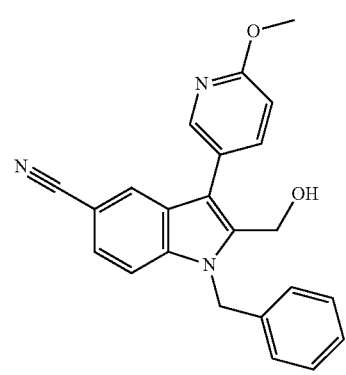
Compound 37-VU0516533-1
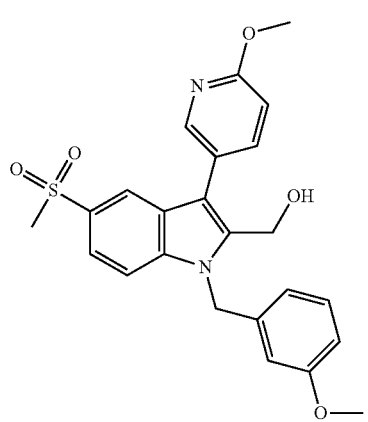
Compound 38-VU0516544-1
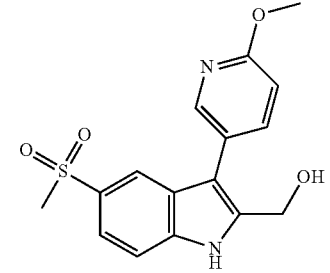
Compound 39-VU0516546-1
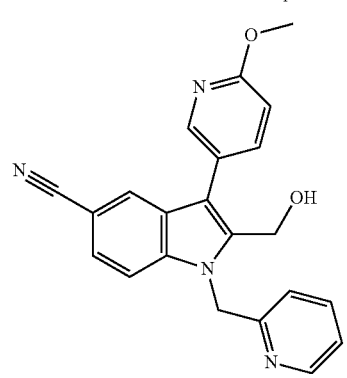
Compound 40-VU0516585-1
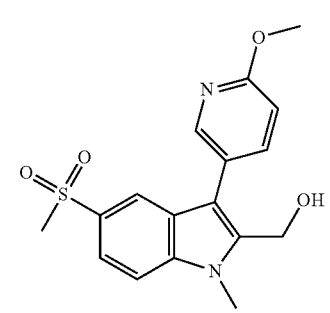
Compound 41-VU0516587-1
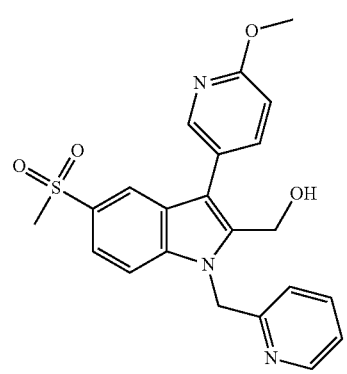

-continued

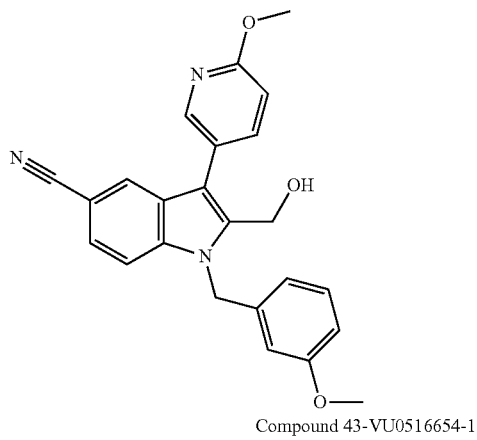

Compound 42-VU0516653-1

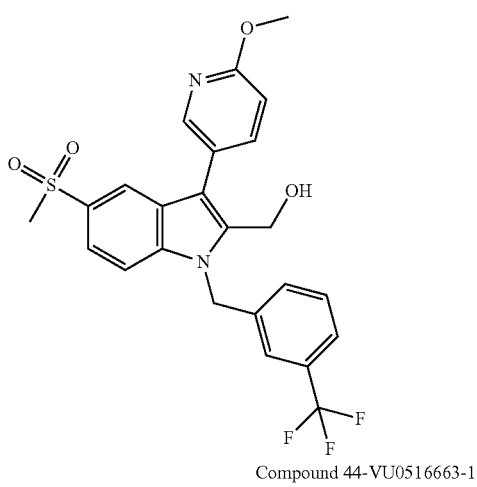

Compound 43-VU0516654-1

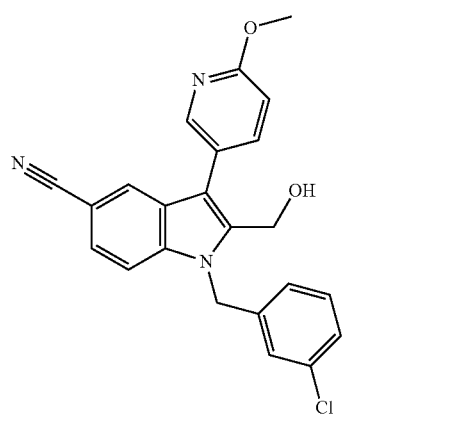

Compound 44-VU0516663-1

Platelet Preparation:
Platelets of 43 μml were added to tubes.
Controls:
2 mL mouse or IgM was added to one control. 2 mL mouse or PAC1 was added to three controls.
Samples:
2 mL of mouse or PAC1 was added to each sample of platelets that contained compounds. 5 mL of compound was added to inhibitor samples. Tyrodes with 1% final concentration, DMSO were added to inhibitor samples with no controls. Each sample was incubated for two minutes. 5.5 mL of PAR4-AP was added to all samples except the no agonist control. Final concentrations of samples=100 mm. Samples were gently mixed and sat at room temperature for 10 minutes. 50 mL of 2% paraformaldehyde was added to each sample and sat at room temperature for 10 minutes. 500 mL of Tyrodes were then added and samples were run of the C6 Accuri.

Experimental Controls

Control 1: Platelets+IgM+100 mm of PAR4-AP.
Control 2: Platelets+PAC-1+1% DMSO+PAR4-AP.
Control 3: Platelets+PAC1+YD-3+PAR4-AP.
Control 4: Platelets+PAC1+Tyrodes.
Each control was done once, with the exception of Control 2 and 4. Samples with compounds were run in groups with a new control for Control 2 and 4 each time. Samples with compounds were ran in groups as follows:
Controls 1, 2, 3, and 4, with compounds A2-H2.
Controls 2 and 4 with compounds A3-H3.
Controls 2 and 4 with compounds A4-H4.
Controls 2 and 4 with compounds A5-H5.
Controls 2 and 4 with compounds A6-H6.
Control 2 and 4 with compounds A7-D7.
Results
Four of the compounds (VU0099704-4, VU0478944-1, VU0478045-1 and VU0478046-1 effectively blocked PAR4-induced platelet activation for subjects with and without the Thr120 variant and one compound (VU0478075-1) blocked PAR4-induced platelet activation for subjects without the Thr120 variant as depicted in FIG. 1. However, FIGS. 2-9 show selected raw flow cytometry data from 28 compounds studied in the screening assay. Screening assay used washed platelets from a single healthy heterozygous (Ala/Thr) donor stimulated with 100 micromolar PAR4-AP and analyzed by flow cytometry for binding of PAC-1 (such binding measures activation of the platelet fibrinogen receptor (integrin aIIbb3)).

CONCLUSIONS

The present invention will aid patients at risk for ischemic cardiovascular disease, such as myocardial infarction, stroke, and peripheral vascular disease. Patients whom possess the PAR4 Thr120 risk are unable to benefit from the current anti-platelet therapy in comparison to patients who lack the PAR4 Thr120 variant in which the following compounds presented in this study would allow effective therapy of all patients, regardless of race or the presence of the PAR4 Thr120 variant.

Accordingly, administration of a compound as described herein can be utilized wherein a suitable dose of the compound is administered to a patient suffering from cardiovascular disease and wherein the compound provides for cardio-protective elements.

Preferred embodiments utilize a method of testing the patient to determine the mutation at position 120, and thereafter providing a corresponding dose of a pharmaceutical composition comprising Formula I, where the dose administered to the patient is modified depending on whether the patient contains the PAR4 Thr120 or PAR4 Ala isoform.

Further embodiments are directed towards a method of treatment comprising a first step of determining the mutation of the patient at position 120; determining a dose of a composition comprising Formula I based upon the mutation of the patient at position 120; administering to the patient the determined dose of composition comprising Formula I.

A further embodiment comprises a method of treatment or use of a composition for treating a patient suffering from coronary heart disease or cardiovascular disease wherein the composition comprises an active ingredient selected from the group consisting of Compositions 1-44 and combinations thereof. In certain embodiments, the method comprises a first step of deterring the mutation of the patient suffering from coronary heart disease at position 120, and determining an appropriate dose of the composition based upon the determined mutation.

BIBLIOGRAPHY

1. Edelstein L C, Simon L M, Montoya R T, Holinstat M, Chen E S, Bergeron A, Kong X, Nagalla S, Mohandas N, Cohen D E, Dong J-f, Shaw C, Bray P F. Racial difference in human platelet PAR4 reactivity reflects expression of PCTP and miR-376c. *Nat Med* 19:1609-16, 2013 (DOI 10.1038/nm.3385; PMID: 24216752).
2. Edelstein L C, Simon L M, Lindsay C R, Kong X, Montoya R T, Tourdot B E, Chen E S, Ma L, Coughlin S, Nieman M, Holinstat M, Shaw C A, Bray P F. Racial variation in the human platelet PAR4 thrombin receptor alters platelet function. *Blood* 124:3450-8, 2014.
3. Tourdot B E, Conaway S, Niisuke K, Edelstein L C, and Bray P F, Holinstat M. Mechanism of race-dependent platelet activation through the protease-activated receptor-4 and GQ signaling axis. *Arterioscler Thromb Vasc Biol* 34:2644-50, 2014.

What is claimed is:

1. A compound selected from the group consisting of a compound of Formula I

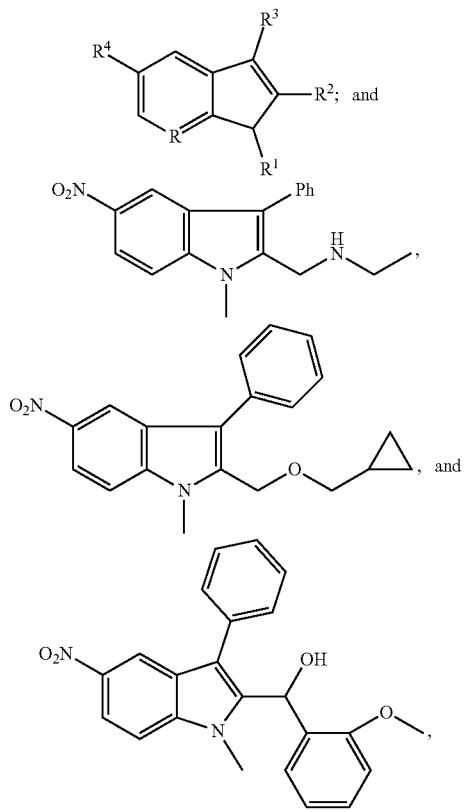

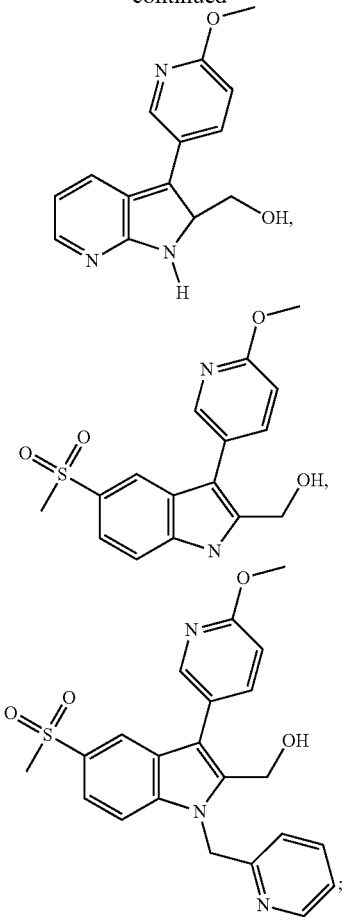

wherein in Formula I:

R is nitrogen or carbon;

$R^1$ is selected from the group consisting of a hydrogen, an alkyl, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl;

$R^2$ is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$alkoxymethyl, a $C_1$-$C_3$ phenylalkoxymethyl, a $C_1$-$C_3$ cyclopropylalkoxymethyl, and a methoxyethoxymethyl; and $R^3$ is a phenyl or a methoxypyridinyl; and $R^4$ is a trifluoromethyl.

2. The compound of claim 1, wherein

R is carbon;

$R^1$ is a methyl;

$R^2$ is a methyl alcohol or a $C_1$-$C_3$ N-alkylmethanamine;

$R^3$ is a phenyl; and $R^4$ is a trifluoromethyl.

3. A pharmaceutical composition for treating a cardiovascular or coronary heart disease comprising a compound selected from the group consisting of a compound of Formula I:

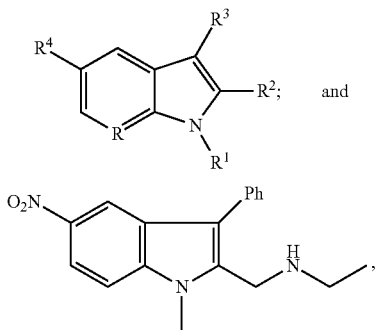

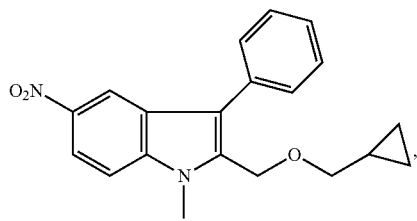

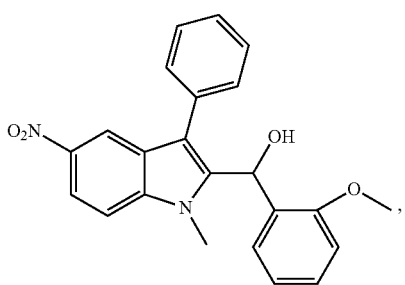

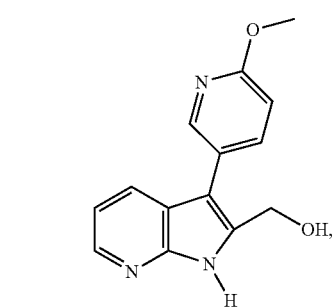

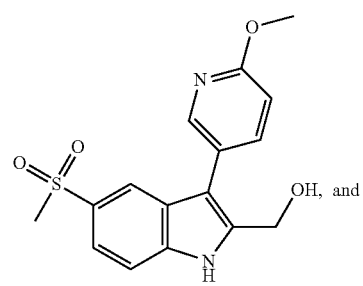

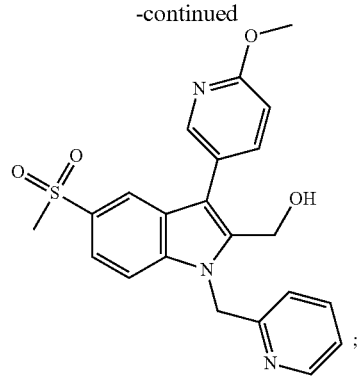

wherein in Formula I:

R is nitrogen or carbon;

R¹ is selected from the group consisting of a hydrogen, an alkyl, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl;

R² is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$ alkoxymethyl, a $C_1$-$C_3$ phenylalkoxymethyl, a $C_1$-$C_3$ cyclopropylalkoxymethyl, and a methoxyethoxymethyl; and R³ is a phenyl or a methoxypyridinyl;

R⁴ is a trifluoromethyl; and a pharmaceutically acceptable carrier.

4. The pharmaceutical composition of claim 3, wherein

R is carbon;

R¹ is a methyl;

R² is a methyl alcohol or a $C_1$-$C_3$ N-alkylmethanamine;

R³ is a phenyl; and

R⁴ is a trifluoromethyl.

5. The pharmaceutical composition of claim 3, wherein the cardiovascular disease comprises a PAR4 isoform.

6. The pharmaceutical composition of claim 3, wherein the PAR4 isoform is Ala120Thr.

7. A method of treatment of a patient having cardiovascular or coronary heart disease comprising administering to said patient an effective amount of a composition comprising a compound selected from the group consisting of a compound of Formula I:

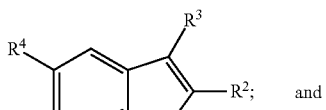

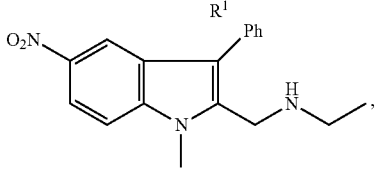

-continued

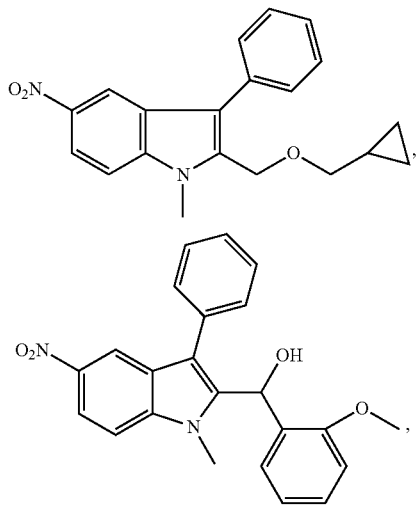

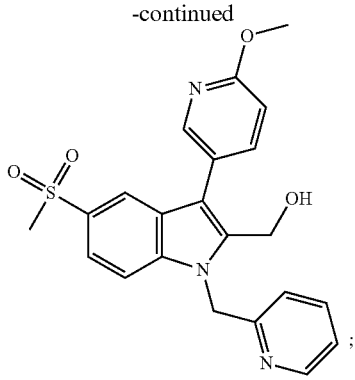

wherein in Formula I:
R is nitrogen or carbon;
R¹ is selected from the group consisting of a hydrogen, a trifluoromethyl, a methyloxyphenyl, a phenyl, a $C_1$-$C_3$ phenylalkyl, a halogenated phenyl, a halogenated $C_1$-$C_3$ phenylalkyl, a trifluoromethyloxy, a trifluoromethyloxyphenyl, and a $C_1$-$C_3$ pyridinylalkyl;
R² is selected from the group consisting of a $C_1$-$C_3$ alkyl alcohol optionally substituted with a $C_1$-$C_3$ alkoxyphenyl, a $C_1$-$C_3$ N-alkylmethanamine, a $C_1$-$C_3$alkoxymethyl, a $C_1$-$C_3$ phenylalkoxymethyl, a $C_1$-$C_3$ cyclopropylalkoxymethyl, and a methoxyethoxymethyl; and
R³ is a phenyl or a methoxypyridinyl;
R⁴ is a trifluoromethyl; and a pharmaceutically acceptable carrier.

8. The method of claim 7, further comprising:
determining the mutation of the patient wherein the PAR4 isoform mutated at position 120; determining a dose of the composition wherein the dose is based upon the mutation of the patient at position 120; and administering to the patient the determined dose of the composition.

9. The method of claim 7 wherein:
wherein R is carbon;
R¹ is a methyl;
R² is a methyl alcohol or a $C_1$-$C_3$ N-alkylmethanamine;
R³ is a phenyl; and
R⁴ is a trifluoromethyl.

10. The method of claim 7, wherein the cardiovascular or coronary heart disease comprises a PAR4 isoform.

11. The method of claim 10, further comprising testing for said PAR4 isoform for a mutation at position 120.

12. The method of claim 10, wherein the PAR4 Isoform is Ala120THR.

* * * * *